US00PP30580P3

(12) United States Plant Patent
Berry

(10) Patent No.: US PP30,580 P3
(45) Date of Patent: Jun. 18, 2019

(54) ***HIBISCUS* PLANT NAMED 'JBG 14002'**

(50) Latin Name: *Hibiscus rosa-sinensis*
Varietal Denomination: JBG 14002

(71) Applicant: Capstone Plants, Inc., Grand Saline, TX (US)

(72) Inventor: James Berry, Edgewood, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 15/998,305

(22) Filed: Aug. 2, 2018

(65) Prior Publication Data

US 2019/0045690 P1 Feb. 7, 2019

Related U.S. Application Data

(60) Provisional application No. 62/605,169, filed on Aug. 3, 2017.

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
See application file for complete search history.

*Primary Examiner* — Annette H Para
(74) *Attorney, Agent, or Firm* — The Webb Law Firm

(57) ABSTRACT

A new and distinct *Hibiscus* plant having large, burnt orange colored flowers with a brownish tint present that last for several days on the plant over a long flowering season.

1 Drawing Sheet

Botanical classification: *Hibiscus rosa-sinensis.*
Varietal denomination: 'JBG 14002'.

BACKGROUND OF THE INVENTION

The present invention comprises a new and distinct *Hibiscus* plant having the varietal name 'JBG 14002'. The new variety is the result of a planned breeding program with the purposes of developing *Hibiscus rosa-sinensis* plants that exhibit pathogen resistance, multi-day flowers with unique coloration, and possess desirable production traits. 'JBG 14002' is the result of a cross conducted in Grand Saline, Tex. between *Hibiscus rosa-sinensis* varieties 'JBG 12005' (female parent, unpatented) and 'JBG 783' (male parent, unpatented). The new variety was selected in October of 2013 in Grand Saline, Tex. and the first asexual reproduction of the new variety was conducted by semi-mature, softwood cuttings in June of 2015 in Grand Saline, Tex. 'JBG 14002' has been trial and field tested and has been found to retain its distinctive characteristics and remain true to type through successive propagations. The present invention has not been evaluated under all possible environmental conditions. The phenotype may vary with variations in environment without a change in the genotype of the plant.

'JBG 14002' is similar to its female parent in having a bronze/brown colored flower center, but differs from its female parent in exhibiting burnt orange colored petals and deeply lobed juvenile foliage. 'JBG 14002' is similar to its male parent in having yellow-toned petals with a dark colored flower center, but differs from its male parent in having a bronze/brown colored flower center and deeply lobed juvenile foliage.

When 'JBG 14002' is compared to *Hibiscus rosa-sinensis* variety 'JBG 14003' (U.S. Plant patent application Ser. No. 15/998,303), both varieties exhibit overlapping petals and a dark colored flower center. However, the dark coloration of the flower center of 'JBG 14003' extends upwards and fades through the throat of the flower, while such extension is not present with 'JBG 14002'.

The following traits distinguish 'JBG 14002' as a new and distinct cultivar from other *Hibiscus* varieties known to the breeder:

1. Large, burnt orange colored flowers with a brownish tint present;
2. Resistance to bacterial leaf spot (*Pseudomonas* spp.);
3. Multi-day flowers; and
4. A strong root system.

DESCRIPTION OF THE DRAWING

The accompanying photographic image illustrates the new variety at approximately one year of age, with the colors being as nearly true as is possible with color illustrations of this type:

FIG. 1 illustrates a close-up view of a flower of the new variety.

DESCRIPTION OF THE PLANT

The following detailed description sets forth the characteristics of the new variety. The color readings and measurements were taken in the summer in Grand Saline, Tex. under natural light on approximately one year old, growing plants in 24.0 cm diameter containers. Color references are primarily to The 1995 R.H.S. Colour Chart of The Royal Horticultural Society of London, 3$^{rd}$ Edition, except where general color terms are used.

PLANT

Time to initiate roots: About 45 days at an average of 24° C.
Time to develop roots: About 50 days at an average of 24° C.

Time to produce a finished flowering plant from a rooted cutting: About 32 weeks in a 24.0 cm diameter container.
Specific disease/pest resistance: Resistance to bacterial leaf spot (*Pseudomonas* spp.).
Heat/cold tolerance: Nothing unusual noted to date.
Drought tolerance: Nothing unusual noted to date.
Plant:
*Type.*—Tropical, ornamental shrub.
*Habit.*—Upright.
*Height.*—92.0 cm at maturity.
*Spread.*—92.0 cm at maturity.
*Vigor.*—Strong.
Rooting vigor: High.
Stem:
*Number per plant.*—10.
*Length.*—Ranging from 23.0-47.0 cm.
*Width.*—1.0-2.0 cm.
*Texture.*—Immature: Smooth. Mature: Vertically ridged.
*Strength.*—Moderate.
*Branch number.*—Moderate; 10.
*Internode length.*—2.0-3.0 cm.
*Color.*—Immature: 143C. Mature: 199A.
*Stipules.*—Number per node: 2. Shape: Linear. Length: 6.0 mm. Width: 1.0 mm. Surface texture: Smooth. Apex: Attenuate. Base: Linear. Margin: Entire. Color: 143C.
Foliage:
*Arrangement.*—Alternate; simple.
*Size of leaf.*—Length: From 6.5-9.0 cm. Width: From 6.0-8.5 cm.
*Shape of leaf* (*generally*).—Ovate.
*Shape of apex.*—Acute.
*Shape of base.*—Rounded.
*Texture* (*both surfaces*).—Smooth.
*Margin type.*—Slightly crenate.
*Color.*—Young leaves: Upper surface: 143A. Lower surface: 143C. Mature leaves: Upper surface: 137A. Lower surface: 146B.
*Veins.*—Venation type: Pinnate. Color: Upper surface: 137C. Lower surface: 137D.
*Petiole.*—Length: 2.0-3.5 cm. Diameter: 3.0 mm. Texture: Smooth. Color: 143C.

FLOWERS

Buds (described approximately 2 days from opening):
*Shape.*—Attenuate.
*Diameter.*—2.5 cm.
*Length.*—4.5 cm.
*Color.*—153C.
Natural flowering season: From spring through fall in Grand Saline, Tex.
Flower type and habit: Single, with overlapping petals.
Fragrance: None observed.
Flowers (described on the first day of opening):
*Number per stem.*—1.
*Overall depth.*—12.0 cm.
*Overall diameter.*—16.0 cm.
*Shape.*—Rotate; regular.
*Lastingness.*—2-3 days on the plant.
*Petals.*—Number: 5. Arrangement: Simple. Length: 9.5 cm. Width: Apex: 10.0 cm. Base: 1.5 cm. Shape: Obovate. Apex: Obtuse. Base: Cuneate. Margin: Entire. Texture/appearance: Upper surface: Velvety. Lower surface: Smooth. Color: When opening and fully opened: Upper surface: 167B at the apex to 46A at the throat. Lower surface: 162C at the apex to 155B at the base.
*Calyx.*—Form: Fused. Overall length: 3.0 cm. Overall diameter: 3.5 cm. Sepals/calyx lobes: Number: 5. Shape: Acute. Apex: Acute. Margin: Entire. Texture: Pubescent. Color: Outer surface: 144A. Inner surface: 144B.
*Epicalyx.*—Length: 1.0 cm. Width: 3.0 mm. Texture: Smooth. Color: 144A.
*Bracts.*—Not present.
*Peduncle.*—Length: 7.5 cm. Diameter: 4.0 mm. Strength: Slightly arching. Angle: 45°. Texture: Smooth. Color: 143C.
Reproductive organs:
*Gynoecium.*—Pistils: Number: 1. Length: 9.5 cm. Stigma: Number: 3 to 4. Shape: Round. Length: 2.0 mm. Diameter: 2.0 mm. Color: 23A. Style: Length: 8.0 cm. Width: 5.0 mm. Color: 37B. Ovary: Shape: Attenuate. Length: 1.0-2.0 cm. Width: 7.0 mm. Color: 154B.
*Androecium.*—Stamens: Number: 84. Position: Just below the stigma on the style. Anther: Shape: U-shaped. Diameter: 2.0 mm. Color: 15A. Filament: Length: 4.0 mm. Width: 1.0 mm. Color: 16B. Pollen: Color: 15A. Amount (generally): Moderate.

SEEDS

Seeds:
*Number.*—From 0 to 20.
*Color.*—200C.
*Length.*—5.0 mm.
*Width.*—5.0 mm.

I claim:
1. A new and distinct variety of *Hibiscus* plant, as is herein illustrated and described.

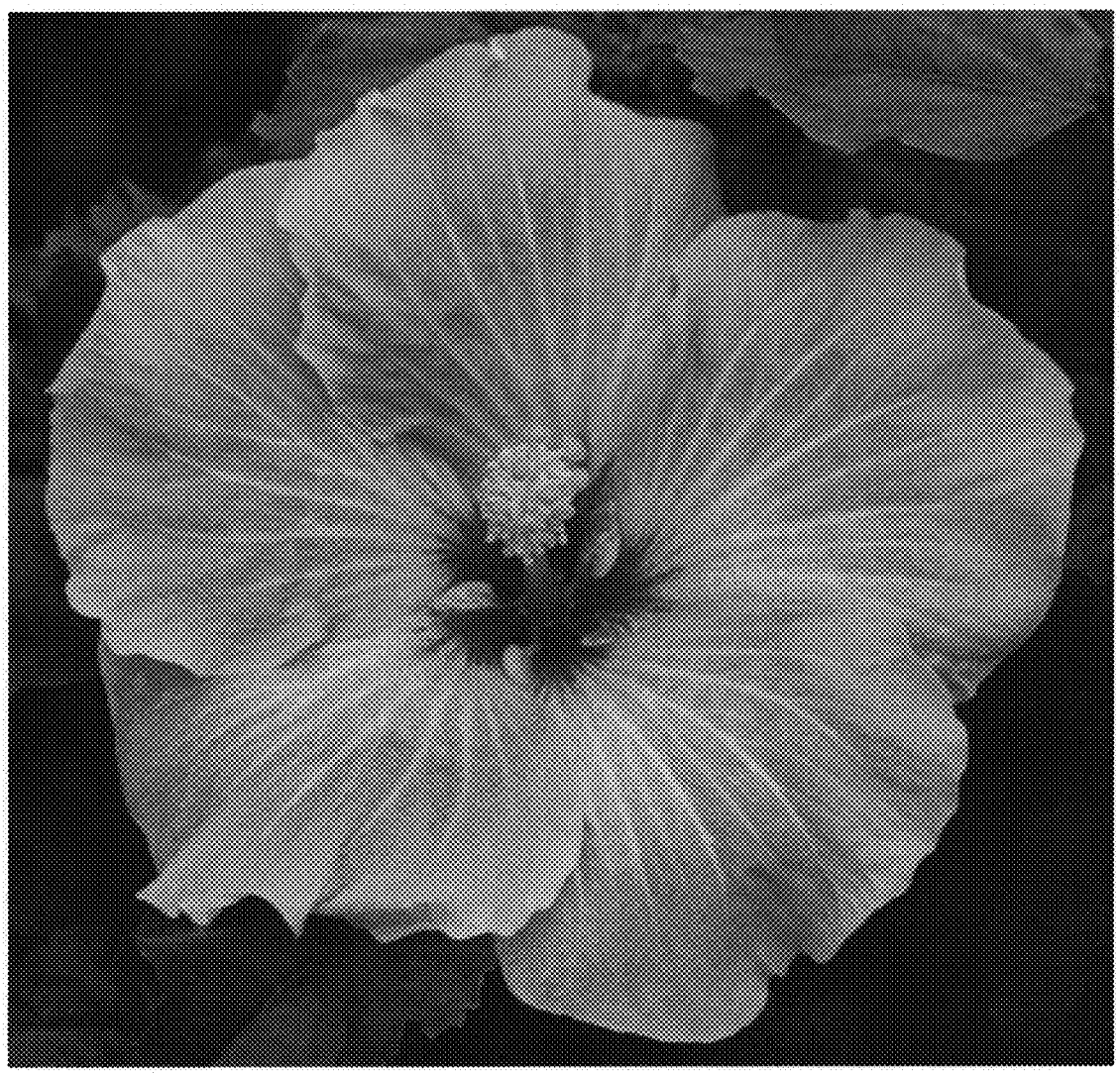

* * * * *